United States Patent [19]
Cheung

[11] Patent Number: 6,005,911
[45] Date of Patent: *Dec. 21, 1999

[54] LARGE AREA ARRAY, SINGLE EXPOSURE DIGITAL MAMMOGRAPHY

[75] Inventor: Lim Cheung, Setauket, N.Y.

[73] Assignee: Trex Medical Corporation, Danbury, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/544,431

[22] Filed: Nov. 17, 1995

[51] Int. Cl.⁶ ....................................................... A61B 6/04
[52] U.S. Cl. ............................................. 378/37; 378/98.8
[58] Field of Search ........................ 378/37, 98.8, 98.21, 378/98.3; 250/367, 368, 361 R, 370.08, 370.09

[56] References Cited

U.S. PATENT DOCUMENTS

| | | | |
|---|---|---|---|
| 4,593,400 | 6/1986 | Mouyen | 378/99 |
| 4,910,405 | 3/1990 | Suzuki et al. | 250/368 |
| 4,933,961 | 6/1990 | Rushbrooke et al. | 378/57 |
| 5,079,423 | 1/1992 | Hagiwara et al. | 250/368 |
| 5,142,557 | 8/1992 | Toker et al. | 378/37 |
| 5,150,394 | 9/1992 | Karellas | 378/62 |
| 5,391,879 | 2/1995 | Tran et al. | 250/367 |
| 5,404,387 | 4/1995 | Hammond et al. | 378/98.3 |
| 5,519,227 | 5/1996 | Karellas | 250/483.1 |
| 5,526,394 | 6/1996 | Siczek et al. | 378/37 |
| 5,563,414 | 10/1996 | Sklebitz | 250/368 |
| 5,572,034 | 11/1996 | Karellas | 250/368 |
| 5,579,360 | 11/1996 | Abdel-Mottaleb | 378/37 |
| 5,584,292 | 12/1996 | Cheung | 378/37 |
| 5,594,769 | 1/1997 | Pellegrino et al. | 378/37 |
| 5,636,299 | 6/1997 | Bueno et al. | 385/15 |

FOREIGN PATENT DOCUMENTS

WO 91/15786   10/1991   WIPO ............................ G02B 6/06

OTHER PUBLICATIONS

Cheung, Lim and Coe, Robert; "Full–Field, Single Exposure Digital Mammography"; Medical Electronics; Oct., 1995; pp. 50–57.

*Primary Examiner*—David P. Porta
*Attorney, Agent, or Firm*—Fish & Richardson P.C.

[57] ABSTRACT

A unique digital imaging device includes the digital imager, a mammography machine including the digital imager, a method for processing the digital image obtained by the digital imager, a local area network (LAN) comprising a number of mammography machines and one or more work stations, and a wide area network (WAN) for transmitting digital images to remote locations. The digital imager according to the present invention comprises a large area, single exposure digital imaging device is provided that allows a number of electronic imagers to be butted together to form an array of electronic imagers large enough to image an entire breast in a single exposure. A preferred embodiment of the digital imager comprises an optical system, such as fiber optic bundles, optically coupled with the surface of the electronic imager. The optical systems may have a surface larger than the electronic sensors, and may be butted together to provide a gap-free imaging surface.

15 Claims, 12 Drawing Sheets

WIDE AREA NETWORK

RADIOLOGIST READING
WORKSTATION

FIG. 13

LARGE AREA ARRAY, SINGLE EXPOSURE DIGITAL MAMMOGRAPHY

BACKGROUND OF THE INVENTION

1. Field of the Invention

The present invention relates to digital radiology and, more particularly, to a large array, single exposure digital mammography machine. The digital mammography machine may process, store access, and transmit data in the same manner as other types of digital image data.

2. Discussion of the Prior Art

According to the American Cancer Society, in 1995 182,000 women will be diagnosed with breast cancer and 46,000 women will die from breast cancer. The ACS estimates that 2,000,000 women will be diagnosed and more than 500,000 women will die of breast cancer in the 1990's. Early breast cancer detection increases the patient's chances of surviving the cancer. Thus, early detection is a major factor in saving the lives of breast cancer patients. Experts agree that a mammogram is the single best means of early breast cancer detection.

Mammography is the radiological examination of the human breast. It is generally accepted that mammography is an effective and reliable procedure in the early detection of breast cancer. Mammography is typically performed using x-ray or other traditional film/screen techniques. However, these techniques do not always provide adequately high-quality images to detect cancer, particularly in the relatively large population of women having radiodense breast tissue (younger women, for example, tend to have radiodense breast tissue). Mammograms require high-quality images because the tissue density between adipose (fatty), glandular, calcified, or cancerous tissue is less diverse than, for example, flesh and bone. Thus, "subtler" contrasts are desirable to distinguish between these types of tissue. Traditional film mammograms have a non-linear response to x-ray exposure. That is, for example, doubling the x-ray exposure of film or halving the breast density, does not result in an image that is twice as bright. As a result, a single traditional film x-ray exposure often do not show the entire tonal range of a patient's breast tissue. Often, a radiologist may take exposures at different energy levels to provide images with different contrasts. This exposes the patient to several doses of x-rays.

Other drawbacks are caused by the poor contrast of film mammograms. One of these drawbacks is that it is difficult to detect masses in patients', having breast implants. A second drawback is that it is difficult to discern between benign and malignant microcalcifications and tumors. This latter drawback results in thousands of unnecessary invasive procedures to remove growths which are later determined to be benign. If a mammogram could allow a radiologist to distinguish more clearly between benign and malignant tissue, many of those procedures would be prevented.

Figure 1:
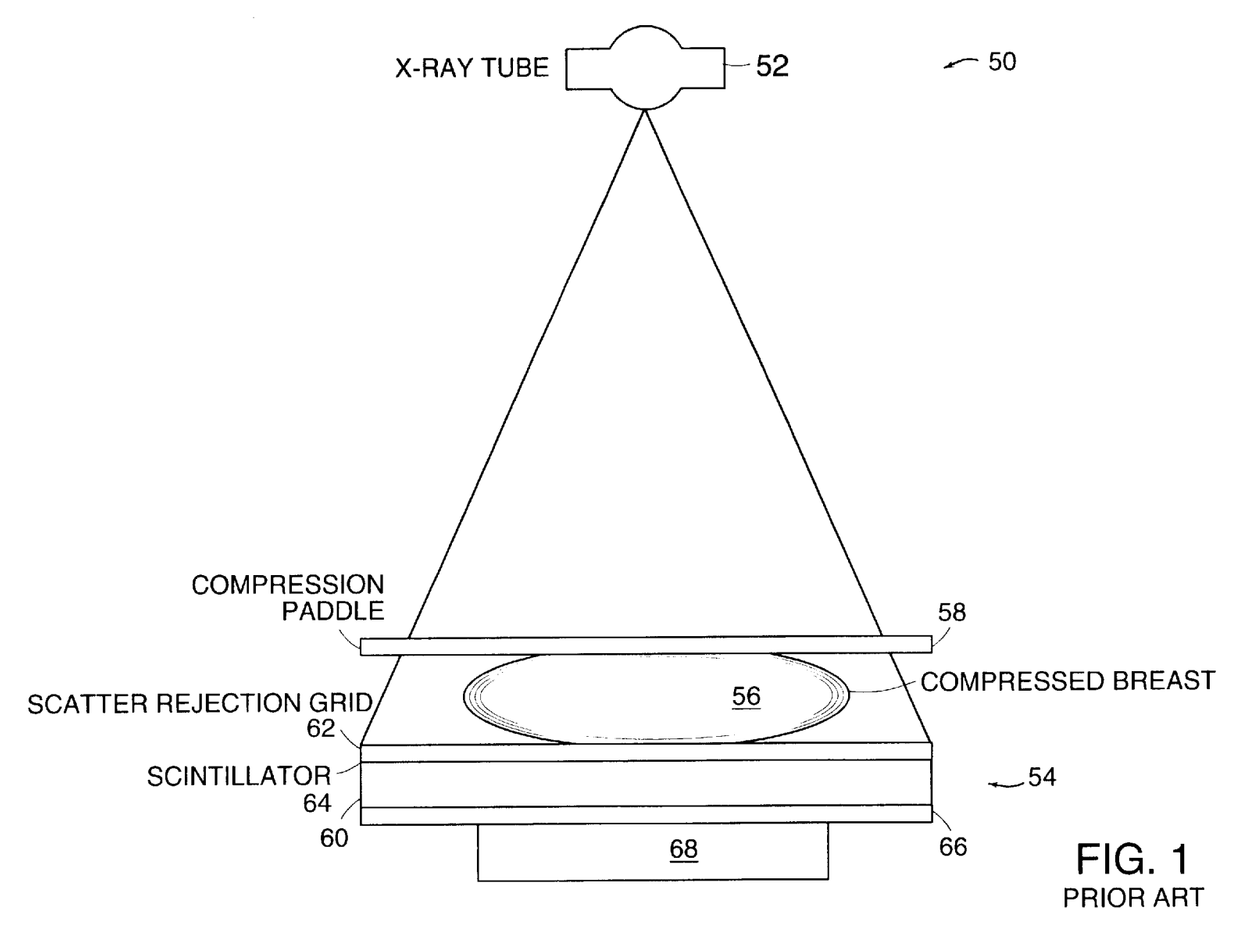
FIG. 1 illustrates a conventional mammography machine using traditional film techniques.

FIG. 1 illustrates a conventional mammography machine using a traditional film technique. The conventional mammography machine 50 has an x-ray tube 52 which emits x-rays and an image receptor 54 which receives the x-ray radiation. During use, a breast 56 is compressed between a compression plate 58 which holds the breast in position, and a bucky tray 60, which sits on top of the image receptor, supports the breast 56 and houses a grid 62. Beneath the grid is a scintillator 64 which generates visible light when excited by x-rays. A film 66 is placed below the bucky tray and scintillator and on top of a radiation detector 68 used for automatic exposure control, such as an ionization chamber or a solid state sensor. X-ray radiation passes through the breast tissue and strikes the scintillator 64. The scintillator generates visible light according to the x-ray striking it. The visible light enters the image receptor and exposes the film. Areas where the x-ray radiation does not pass through the tissue result in a light area on the film indicating a mass or other x-ray blocking body. After the film is exposed, it is developed before it may be viewed.

Digital mammography which employs a solid state electronic imager in place of film is an emerging technology in the detection of breast cancer. Digital mammography has advantages over the traditional types of mammography. The National Cancer Institute recently sponsored workshops on breast imaging and digital mammography. One conclusion from these workshops is that digital mammography has great potential for use in the diagnosis and screening of breast cancer and for use during invasive procedures on breast cancer patients. Digital mammography offers:

1. Shorter procedure times, resulting in improved patient comfort and less likelihood of image blurring due to patent motion (including involuntary motions such as heartbeats and breathing);
2. improved image quality due to (a) larger dynamic range and linear x-ray exposure response (linear latitude) of electronic imaging techniques, and (b) computer-aided visualization. This improved image quality permits clearer imaging of patients having breast implants and a greater likelihood of distinguishing between benign and malignant growths;
3. decreased healthcare costs because digital mammograms provide early detection; early breast cancer detection typically results in lower treatment costs. Also, the improved image may reduce the number of unnecessary procedures because of potentially better visualization of suspicious morphology; and
4. lower radiation exposure because of the lower radiation-per-image requirements for the shorter exposure time, and the resultant accurate images reduce the need to re-take an image or take several exposures.

Figure 2:
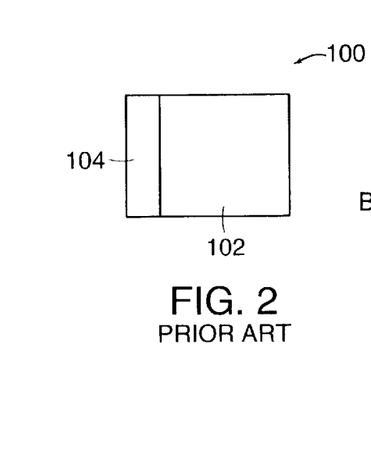
FIG. 2 is a block diagram illustrating a conventional charged coupled device.

Digital mammography currently has several shortcomings. One major shortcoming is that most known digital mammography machines cannot take an image of an entire breast in one exposure. One reason for this is because the electronic imagers for capturing the image are small and cannot be arranged together to provide a gap free imaging surface large enough to image an entire breast in a single exposure. One well known electronic imager is a charged coupled device (CCD). FIG. 2 illustrates a typical CCD 100. A CCD is typically a device having an imaging surface area 102 no larger than 1"×1" and containing up to 2000×2000 pixel elements. This one square inch area is not sufficient to image an entire breast. Current CCD technology uses at least one side of the CCD 100 for circuitry 104 for peripheral components, such as amplifiers and serial registers. These peripheral components on the side of the CCD 100 prevent CCDs from being butted together on four sides without a significant gap in the imaging surface. Thus, the first digital mammography machines were small devices used during invasive procedures to locate suspicious masses during needle localization or core biopsy procedures. The small imaging surface of CCDs has prevented widespread use of digital mammography.

Digital mammography also faces severe technical challenges. Soft-tissue breast imaging has the most stringent imaging requirements of all radiological imaging. Two reasons for this are the slight difference in densities between the tissue types found in breasts (adipose, glandular, calcified, and cancerous) and the relatively small size of breast tumors in their initial stages. As a result, mammography requires very fine pixel dimensions (e.g., less than 40 microns) and a high contrast dynamic range (14 bits, i.e., $2^{14}$ or 16,384 tone levels) over a large area (i.e., 24 cm×30 cm). The American College of Radiology recommends an image resolution of 11 to 13 line pairs per millimeter. This means that the image should be sharp enough to distinguish between 11 to 13 pairs of white and black lines in a one millimeter space.

Several digital mammography machines are commercially available. Because of the large number of pixels needed to image an entire breast and electronic detector size limitation described above, these mammography machines use one of two systems to image an entire breast.

The first system is a scanned beam system. In a scanned beam system, the electronic imager is mechanically scanned along the patient's breast as beams of radiation are transmitted towards the imager at each position, until the entire breast is imaged. The x-ray beam is collimated into a long thin line and scanned slowly across the breast and a thin, linear scintillator-coupled CCD array is synchronously scanned beneath the breast in perfect registration with the beam in order to receive the radiation. This method has several drawbacks. The scan time is long, which is uncomfortable for the patient and increases the likelihood of image discontinuity due to patient movement during the procedure (including involuntary motions such as breathing and heartbeats), adversely affecting the image quality. The patient may be exposed to radiation longer than necessary for imaging, which is undesirable. The mechanical devices necessary to maintain the beam/CCD array synchronization is complex and requires a special support system. Therefore, this device cannot be used interchangeably with standard film/screen mammography machines.

Also, the x-ray tube is on for a prolonged time period, and is subjected to high heat loading. A molybdenum x-ray target typically used in mammography will melt under this high heat load. To overcome this heat loading problem, a tungsten x-ray target is used. Tungsten targets operate at suboptimal high kV ranges (near 40 kVp), which detrimentally affects the contrast between adipose (fatty), glandular, or calcified breast tissue. As noted above, a low image contrast is unsuitable for imaging soft tissue such as breasts.

The second system is a multiple exposure system. In a multiple exposure system, the electronic imagers are positioned over various locations of the breast and then exposed to radiation at each location. This is repeated until the entire breast is imaged. This method also has several drawbacks. The mechanics of this device preclude it from being used interchangeably with standard film/screen mammography machines. To insure that the entire breast is imaged, some overlap between exposed locations occurs. The overlapped areas are exposed to twice as much radiation as in a standard mammogram. This method also has the disadvantage that the result is several images, not a single image, of the breast. Complicated image processing and registration techniques, such as "stitching", are required to view the image.

Therefore, it is an object of the present invention to provide a digital mammography machine that can image an entire breast in a single, low radiation exposure.

It is another object of the present invention to provide a digital mammography machine that can be used in existing film/screen mammography machines, without significant alteration to the machine, or complex mechanical devices.

It is a further object of the present invention to provide a digital mammography machine that uses conventional x-ray targets and optimal energy levels.

It is an even further object of the invention to provide a digital mammography machine which provides improved image quality, allowing clearer images of patients having breast implants.

It is yet over another object of the present invention to provide a digital mammography machine having sufficient contrast to distinguish between microcalcifications and surrounding breast tissue.

It is yet another object of the present invention to provide a digital mammography machine that allows a single technician to control a plurality of mammography machines from a remote control station.

It is yet an even further object of the invention to provide a digital mammography machine that allows the image to be transmitted over telephone lines or other communication channels.

SUMMARY OF THE INVENTION

These and other objects of the invention are provided by a mammography machine according to the present invention. The invention comprises a unique digital imager, a mammography machine including the digital imager, and a method for processing the digital image obtained by the digital imager. The digital image may be transmitted on a local area network (LAN) comprising a number of mammography machines and one or more work stations, and a wide area network (WAN) for transmitting digital images to remote locations.

The digital imager according to the present invention comprises a large area, single exposure digital imaging device which allows a number of electronic imagers to be butted together to form an array of electronic imagers large enough to image an entire breast in a single exposure. A preferred embodiment of the digital imager comprises an optical system, such as fiber optic bundles, optically coupled with the surface of the electronic imager. The bundles may have a surface larger than the electronic sensors, and may be butted together to provide a gap-free imaging surface.

The mammography machine according to the present invention may be a conventional mammography machine having the digital imager constructed in the shape of a conventional x-ray film cassette. The digital imager is loaded into the mammography machine in a similar manner as a conventional film x-ray.

The digital mammography provides a clearer image having better contrast than provided by a film mammogram. The present invention provides clear imaging of patients having breast implants and provides images which allows; and radiologists to better visualize the breast morphology.

Because the image is in digital form, the image is available seconds after it is taken, unlike film, which must be developed. The digital image may be processed, stored, accessed, and transmitted in the same manner as other digital data. For example, the digital image data may be transmitted on a local area network (LAN) or wide area network (WAN).

BRIEF DESCRIPTION OF THE DRAWINGS

The present invention is described with reference to the following figures.

DETAILED DESCRIPTION OF A PREFERRED EMBODIMENT

1. A Single Exposure, Full Field Digital Array

Figure 3A:
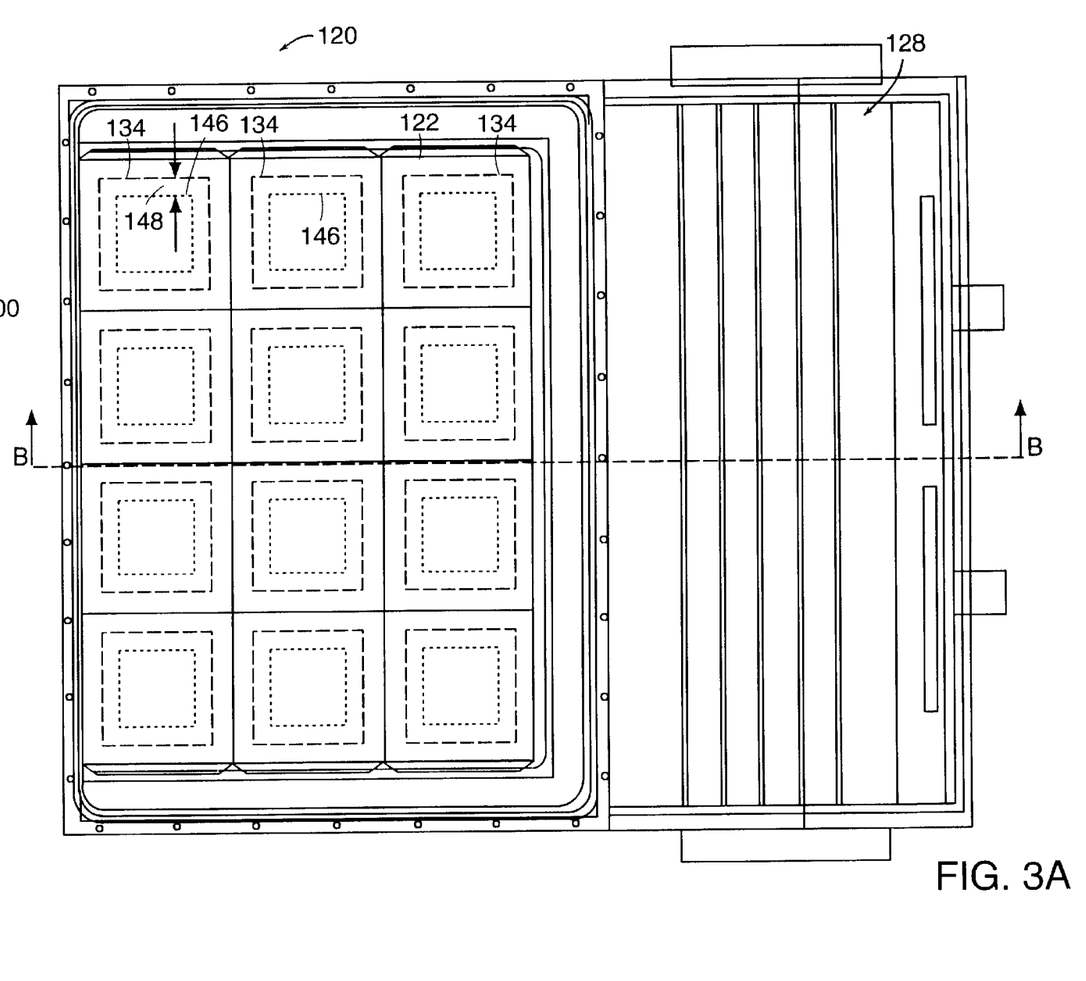
FIG. 3A is top elevational view of a preferred embodiment of a single exposure, large area array imager according to the present invention.
Figure 3B:
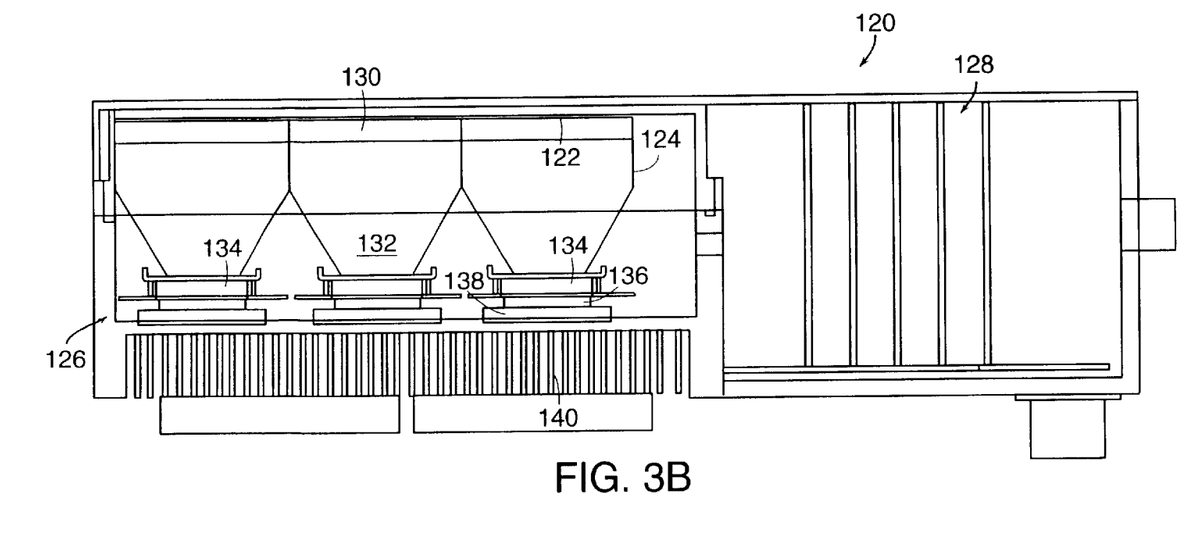
FIG. 3B is a cross-sectional view of the image of FIG. 3A taken along line B—B.

FIGS. 3A and 3B illustrate a preferred embodiment of a single exposure, large area imager array 120. The imager array is possible by a novel technique for butting together a number of electronic imagers, such as those shown in FIG. 2, without a gap in the image. The preferred embodiment employs CCD (charged coupled device) sensors, but a person skilled in the art understands that other electronic imagers, such as amorphous polysilicon flat panel detectors, selenium storage plates, zinc cadmium telluride sensors, and the like may be used as well.

The single exposure, large area imager array 120 provides an image receptor surface 122 having no significant gaps. The imager array comprises an image receptor 124, a thermoelectric cooling arrangement 126, and receptor electronics 128. The image receptor 124 comprises a scintillator 130, an optical system 132, such as a fiber optic bundle, and an electronic imager 134, such as CCDs. The thermoelectric arrangement comprises a cold finger 136, a thermoelectric cooler 138, and a number of heat sink fins 140. The receptor electronics 128 are discussed in more detail in relation with FIG. 5.

A. The Image Receptor

As seen in FIG. 3A, a number of electronic imagers 134, such as CCDs, are arranged in an array. FIG. 3A shows twelve electronic imagers 134 butted together. The image receptor surface 122 has no significant gaps. This surface is created by using an optical system 132 (FIG. 3B), such as coherent fiber optics bundles in the form of a beam expander, optically coupled to the surface of the electronic imagers 134. This provides a large area digital imaging array 120 having an image receptor surface 122 without any significant gap.

Figure 4:
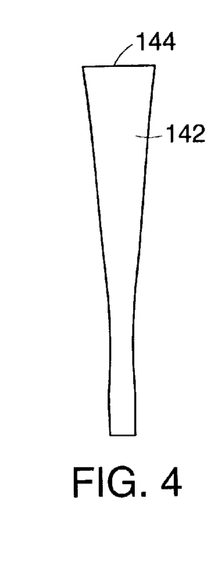
FIG. 4 is a front elevational view of one optical fiber for a preferred optical system according to the present invention.

The optical receiving area of the imagers coupled to the fiber optics is enlarged from the surface area of the imagers 134 to the image receptor surface 122 of the imager array 120. As seen in FIG. 4, each optical fiber 142 in the bundle 124 is tapered from top to bottom. The fiber optics bundle may be machined precisely so that the periphery of the fiber optics front surface entrance aperture 144 is mapped to the interior of the electronic imager 134 with no dead zone within the entrance aperture. This allows multiple electronic imager/optical fiber building blocks to be butted in two dimensions to build active imaging areas of arbitrary size with no gaps between the modules.

The fiber optic bundle 132 does not extend to the very edges of the electronic imager 134. Rather, pixels at the edge of the electronic imager 134 are not used. This insures that every pixel on the image receptor surface 122 is received by an electronic imager 134. Referring to FIG. 3A, the surface area of the electronic imagers 134 is shown in large dashed lines. The area of the optical system 132 where it couples with the electronic imager 134 is shown in smaller dashed lines 146. Note that a space 148 exists between the surface area of the electronic imager 134 coupled with the optical system 132 and the overall surface area of the electronic imager 134.

A lens system may be used instead of a fiber optics bundle as the optical system. This system is inferior, however, because at a magnification level of two, for example, fiber optics collect light approximately four times better than a lens system. This difference is even more marked at off-axis incident angles because lens systems suffer from a steep $\cos^4 \theta$ loss of optical efficiency away from the optical axis. Thus, a fiber optics bundle is the currently preferred optics system.

When a breast is imaged, the x-rays passing through the tissue strike the scintillator 130, which creates visible light. The visible light is transmitted through the optical system 132 and is optically coupled to the electronic imager 134. The visible light is detected by the electronic images, which generates an electronic signal representing the visible light.

B. The Thermoelectric Cooling Arrangement

Referring to FIGS. 3A and 3B, the digital imager array 120 is thermally stabilized at low temperature to further reduce system noise to a level limited only by quantum statistical photon fluctuations. That is, the electronic imagers 139 should not detect any light energy when not exposed to light. However, some noise energy is detected due to electron pairs thermally generated by room temperature heat. This noise—called "dark noise"—is undesirable. In order to reduce this "dark noise", the electronic imagers 134 are cooled and maintained at a constant temperature, such as−25° C., to reduce the thermally generated electron pairs. The electronic imager 134 is maintained at a constant temperature in order to fix the current due to the thermally generated electron pairs. By keeping this current fixed, the dark noised is maintained at a constant predictable level. To this end, the thermoelectric cooling arrangement 126 is provided. The cooling arrangement includes a cold finger 136, a thermoelectronic cooler 138, and a number of heat sink fins 140. The cold finger 136 provides a heat conductive path between the electronic imager and the thermoelectric cooper. The cold finger preferably is a material having high thermoconductivity, such as cooper. The thermoelectric cooler 138 is a conventional thermoelectric cooling device and is connected to an external temperature control (described below with reference to FIG. 7) and cools or heats the electronic imager 134 to which it is connected. The bottom of the thermoelectric cooler generates heat. A number of heat sink fins 140 are provided to dissipate the heat generated by the thermoelectric cooler.

The entire imager array 120 must be protected from moisture, which may corrode the imager array components. Thus, it is best to seal the imager array 120. To seal the imager, it is preferable to use a metal, particularly because plastic enclosures are prone to leakage. A preferred metal is beryllium because it provides a good water vapor barrier and is radio transparent (e.g., does not show up on a x-ray). Before the array is sealed, it may be packed with dry nitrogen to keep the components dry.

C. The Image Receptor Electronics

Figure 5:
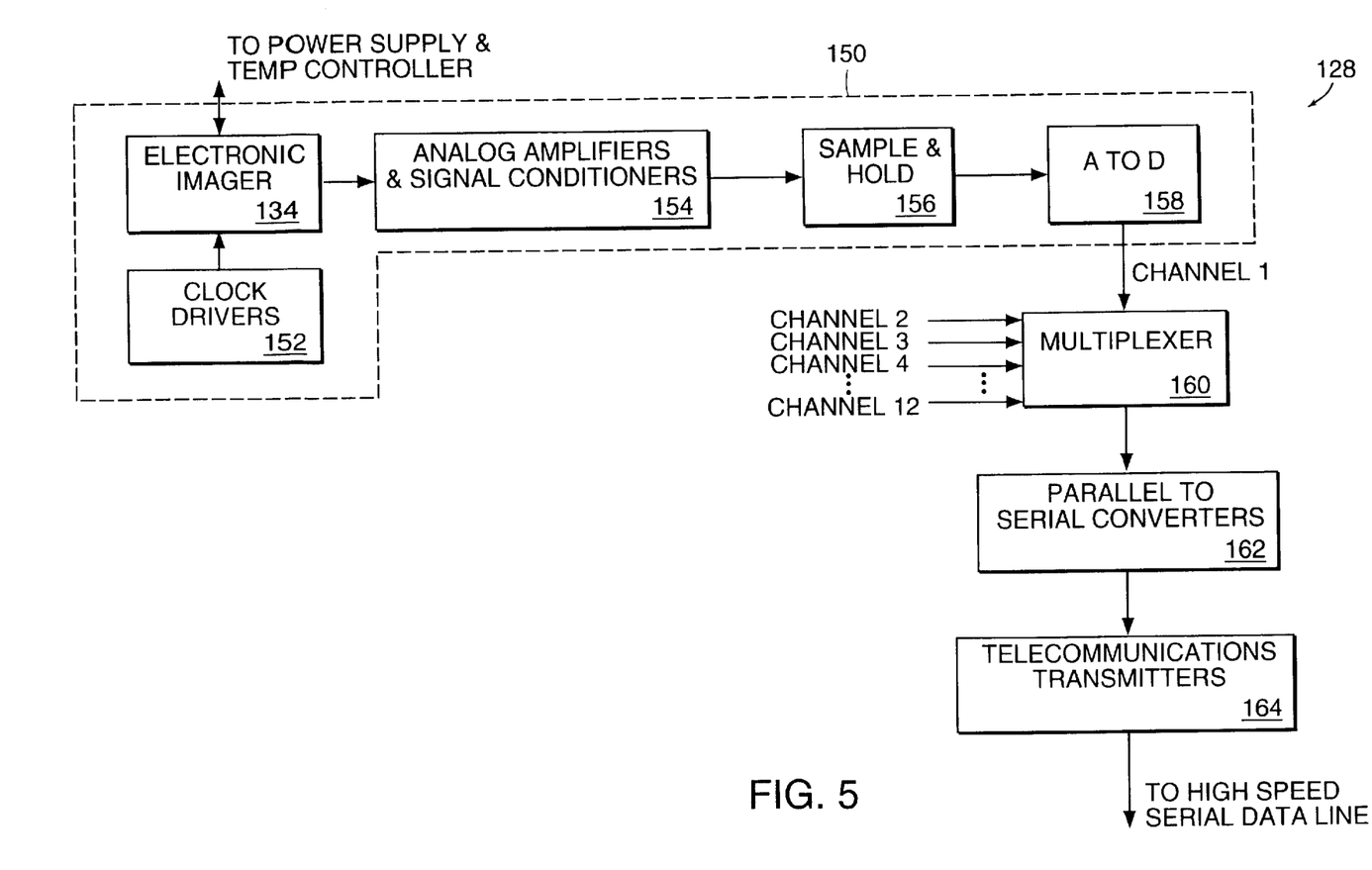
FIG. 5 is a block diagram of a preferred embodiment of image receptor electronics according to the present invention.

FIG. 5 is a block diagram of the image receptor electronics 128. Each electronic imager 134 comprises a single channel 150. If the digital imager array 120 comprises twelve electronic imagers 134, there are twelve channels. Each channel includes an electronic imager 134, clock drivers 152, an analog amplifier and single conditioner circuit 154, a sample and hold 156, and an analog to digital convertor 158. The clock drivers 152 are connected to an input of the electronic imager 134 for timing and refreshing the electronic imager 134. The output of the electronic imager is provided to the input of an analog amplifier and signal conditioner circuit 145. This circuit amplifies the signal and adjusts it to the appropriate voltage range for processing by the electronics. The output of the analog amplifier and single conditioner circuit 154 is applied to the input of a sample and hold 156, which measures the amplitude of the analog signal at predetermined times and provides the samples to the input of the analog-to-digital convertor 158. The analog-to-digital convertor changes the analog signal into digital form.

Each channel outputs a digital signal to a multiplexer 160, which combines data from each channel, e.g., each electronic imager 134 in the array 120. The output of the multiplexer 160 is provided through a parallel to serial convertor 162, which places the digital data into serial form. The serial data is provided to the input of a telecommunications transmitter 164 which packages the data into a form for transmission along a serial data line. A presently preferred telecommunications transmitter is a TAXI chip made by Advance Micro Devices. This chip puts the data information into packets and provides error corrections such as a cyclical redundancy check (CRC).

Figure 6:
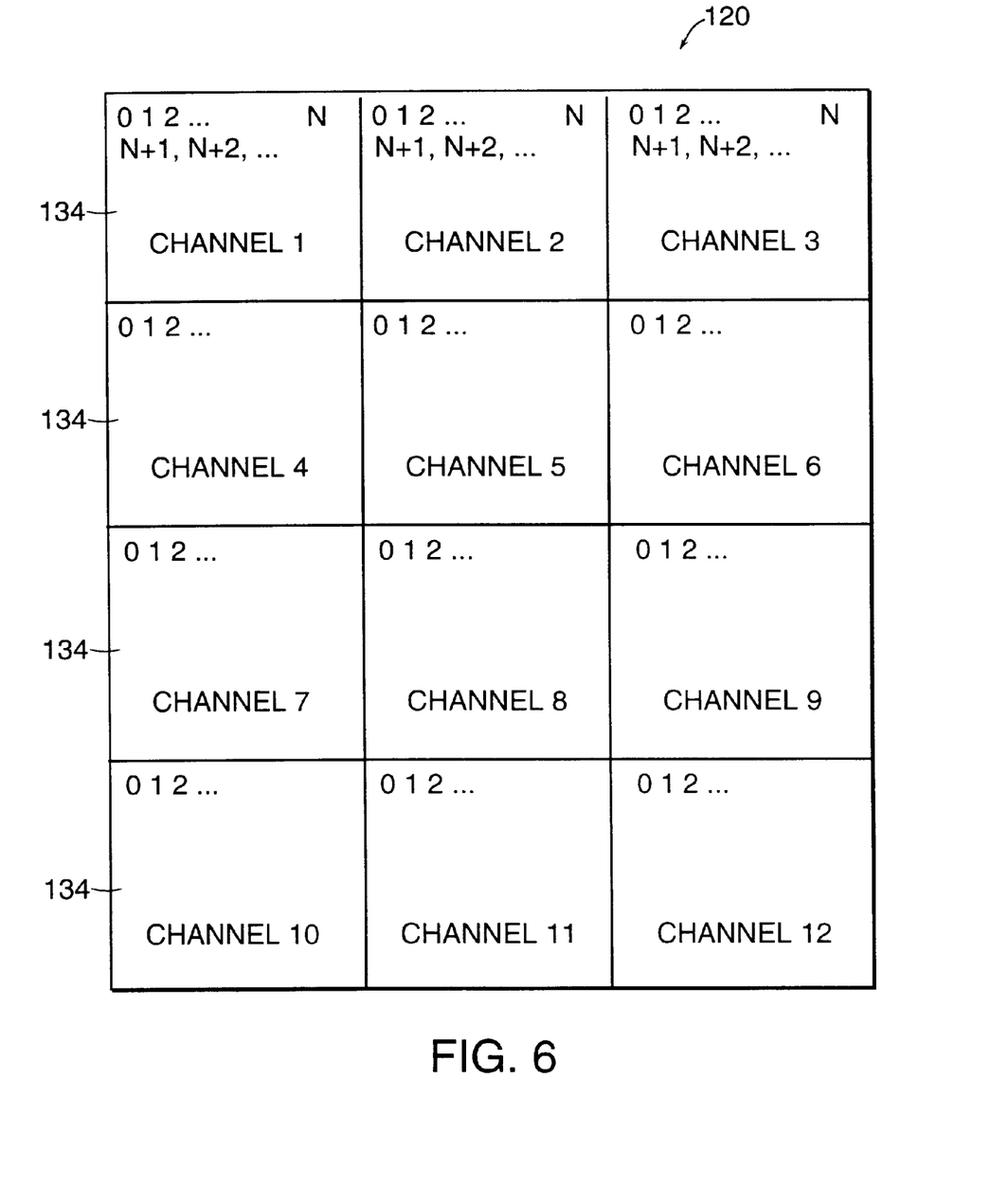
FIG. 6 is a diagram illustrating a method of multiplexing information from the electronic images.

FIG. 6 illustrates how the channels are multiplexed by the multiplexer 160. Each pixel of each channel (e.g., each electronic imager 134) is associated with a number. For example, a first pixel in a first line is identified as pixel 0, the next pixel in the first line is identified as pixel 1, the next is pixel 2, and so on. The electronic imager represents the visible light received by each pixel into an electronic signal. These signals are taken from the electronic imager and presented to the multiplexer 160 in the following way. First, pixel 0 from channel 1 is presented to the multiplexer 160. Next, pixel 0 from channel 2 is presented, then pixel 0 from channel 3, and so on until pixel 0 from channel 12 is presented. Then pixel 1 from channel 1 is presented, and so on until pixel 1 from each channel is presented to the multiplexer. That is repeated until every pixel is presented.

The image receptor electronics 128 convert the analog signal into a digital signal before the signal leaves the digital array 120 for further processing. The digital signal preferably has a 14 bit resolution; that is, having $2^{14}$ or 16,384 gray tones. By converting the signal into digital form before it leaves the digital imager 120, the signal is more immune to electro-magnetic interference and allows the telecommunications transmitters 164 to add error correction codes to reduce the likelihood that the information will be corrupted, distorted, or interfered with.

The resulting image contains all of the information, but cannot be viewed directly. This is because of (1) optical distortion; (2) photometric distortion; and (3) unused sensor pixels framing each building block. The optical distortion is caused by spatial irregularities in the fiber optics bundle. Photometric distortions are due to imperfections in each pixel's response characteristics. The unused pixels framing each sensor are unused because the optical mapping is deliberately undersized to capture the full image at the entrance aperture without dead zones, as described above. A digital imager according to the present invention may image a 50/50 adipose-glandular breast in less than one second (e.g., less than one second radiation exposure). The resulting image may be viewed after image processing is performed to convert the resulting image into an accurate representation of the patient's breast. This process, described below, provides a digital image of the breast in about 10 seconds. This is significantly faster than the time needed to view traditional film, which requires the film to be developed after being exposed.

The digital sensor is capable of imaging an entire breast in a single, short radiation exposure. No scanning or stepping of the sensor or x-ray source is necessary, thus, the patient exposure time is minimized.

2. A Digital Mammography Machine

Figure 7:
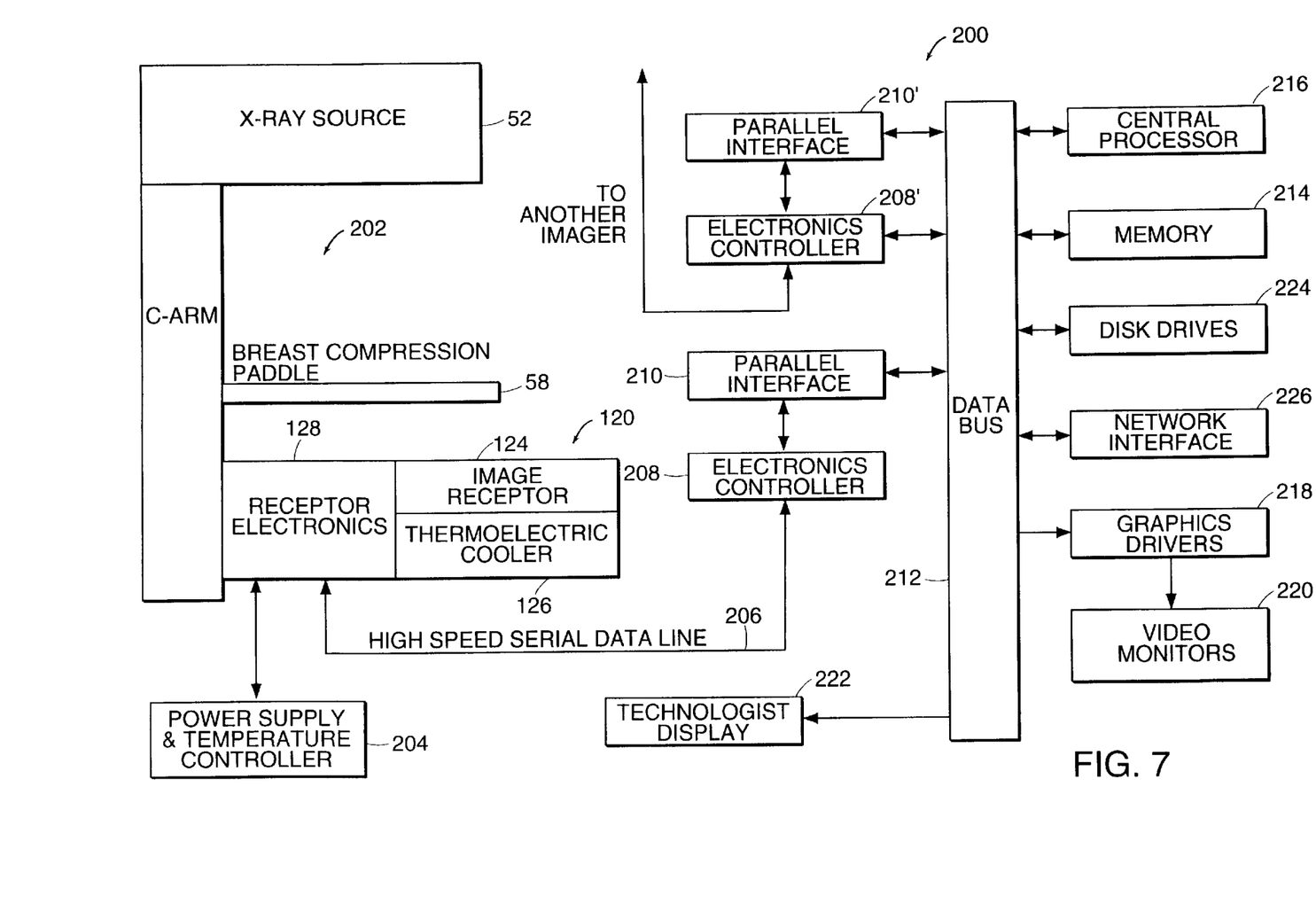
FIG. 7 is a block diagram of a preferred embodiment of a mammography machine according to the present invention.

The array described may be used in existing mammography machines. For example, the digital imaging array 120 may be placed in a Bennett X-Ray Contour™ mammography machinery (or other machines by manufacturers with minor modifications in software). FIG. 7 is a block diagram of a mammography machine 200 with a breast support 202 containing a digital imaging array 120 according to the present invention. The digital imaging array 120 is preferably constructed in a removable cassette similar in size and shape to a conventional x-ray film/screen cassette. The digital imaging array may be used in existing mammography machines without altering the existing mammography machine.

As illustrated in FIG. 7, a mammography system 200 has an x-ray tube 52 that emits x-rays and an image receptor 120 which receives the x-ray radiation. A breast is compressed by a compression plate 58 and a bucky tray which supports the breast and houses a grid. Instead of a film, a cassette containing a digital imaging array 120 as described above is placed below the bucky tray. The image receptor electronics 128 may be connected to a power supply and temperature control circuit 204. This circuit provides electrical biases to the imager components and provides power to the electronic imagers 134 (FIG. 3B) and thermoelectric cooler 126. The temperature controller reads the temperature of each electronic imager and regulates the temperature of each electronic imager individually using closed loop digital servo control circuitry. A processor, such as a digital microprocessor, may be used in a well-known manner to monitor the temperature of each individual thermostat and compute the correcting current and voltages to maintain the device at a constant temperature.

Figure 8:
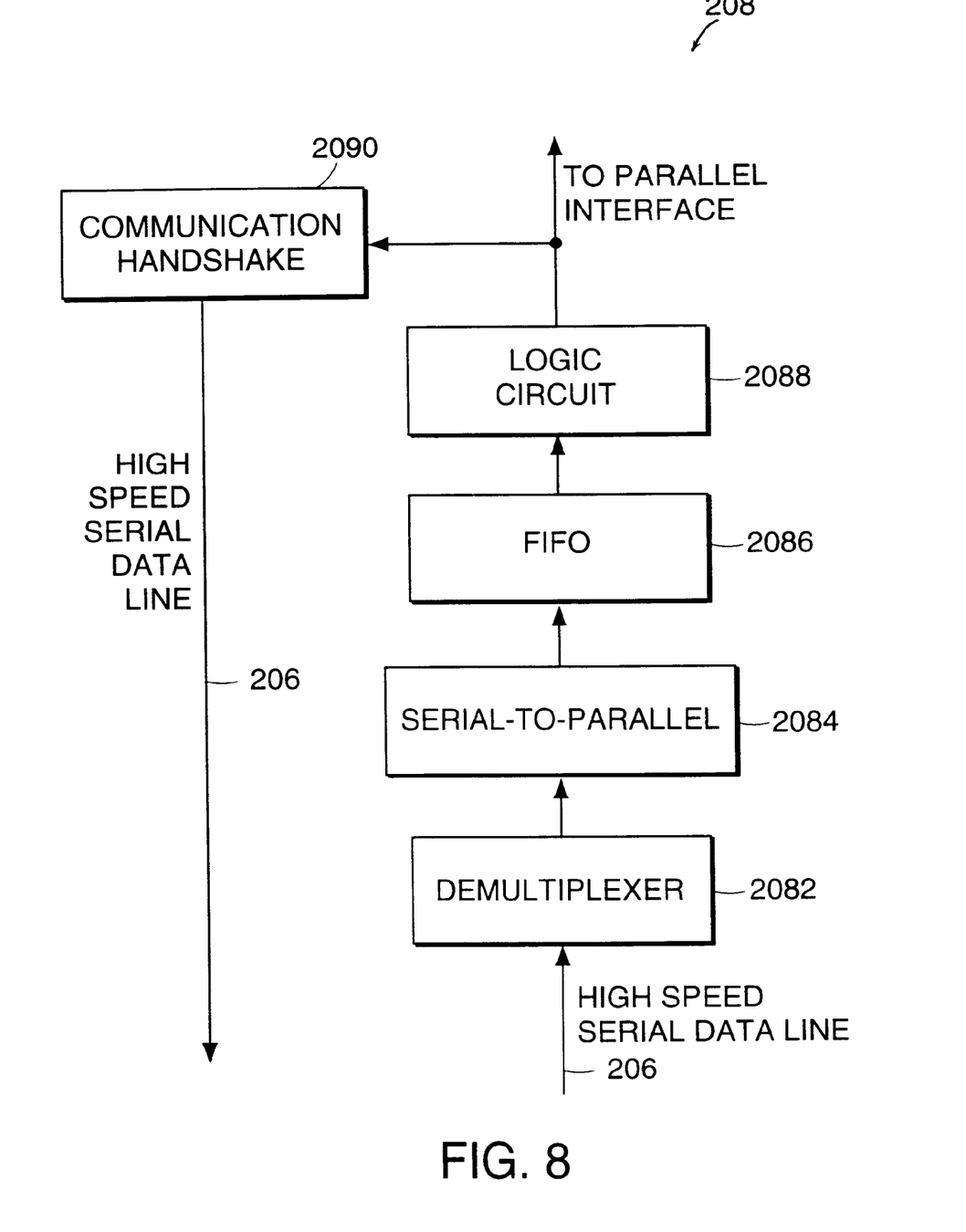
FIG. 8 is a block diagram of a preferred embodiment of an electronics controller according to the present invention.

One major difference between digital imaging and film imaging is that the image is instantaneously available for processing. As seen in FIG. 7, the receptor electronics 128 are connected to a high speed serial data line 206 for transmitting the digitized image data to an electronics controller 208. FIG. 8 is a block diagram of a preferred embodiment of an electronics controller 208 according to the present invention. The electronics controller 208 receives the data in a serial format. The data is received by a demultiplexer 2082, which demultiplexes the data into separate channels. That is, the data is presented to the electronics controller 208 multiplexed as described with reference to FIG. 6 above. The digital data is separated into the individual channels. The demultiplexed data is presented to a serial-to-parallel convertor 2084, which converts the data from a serial format into a parallel format. Preferably, the data is converted into a number of 16-bit parallel words.

The data words are presented to a first-in-first-out memory buffer 2086, which stores the data. An on-board logic circuit 2088 sorts the data into an order that corresponds to the digital image. This means, referring to FIG. 5, for example, the data may be arranged as follows: channel 1, pixel 0 through pixel N (e.g., the first line of channel 1); followed by channel 2, pixel 0 through pixel N (e.g., the first line of channel 2), followed channel 3, pixel 0 through N. The next pixel would be channel 1, pixel N+1 (e.g., the second line of channel 1), until the end of that line of channel 1. Next is channel 2, pixel N+1. That line is followed by channel 3, pixel N+1, etc., until every line of every channel is arranged.

The electronics controller 208 may also contain a communication handshake circuit 2090, which allows the imager array 120 to coordinate with the x-ray source 52 (FIG. 1) and to provide a safety interlock preventing the x-ray machine from being activated when the imager array 120 (FIGS. 3A and 3B) is not yet ready. At the beginning of an x-ray exposure, for example, the x-ray generator in the x-ray source may send a signal to the electronic imagers which instruct the clock drivers 152 (FIG. 5) to start refreshing the electronic imagers 134 (FIG. 5). An "x-ray on" signal may be provided by the x-ray generator in the x-ray source during the x-ray exposure in order to start the charge integration, data read out, and data transmission cycles. Once the data is arranged in the proper order, it may be transmitted along a data bus 212 (FIG. 7) directly into a memory 214 using direct memory access or it may be sent to a central processor 216 for additional processing. The image may also be presented to a graphics driver 218 for display onto a video monitor 220 or it may be sent to a technologist's display 222 so that the radiological technologist may view the image.

The system may control a number of mammography machines and a number of electronics controllers 208' and parallel interfaces 210' may be connected to the data bus 212 so that a number of mammography machines may be controlled by the central processor 216. The central processor 216 may be configured to perform the switching and sequencing functions to provide multiple mammography machines. The data transmission period of an image following x-ray exposure typically takes 6 seconds. The chance of a data transmission conflict is small for a configuration having three mammography machines, for example.

A disk drive 224 may be provided on the data bus 212 for holding data, such as optical data, which may be useful to the radiologist. A network interface 226 may be provided to connect the mammography machine to a local area network.

Figure 9:
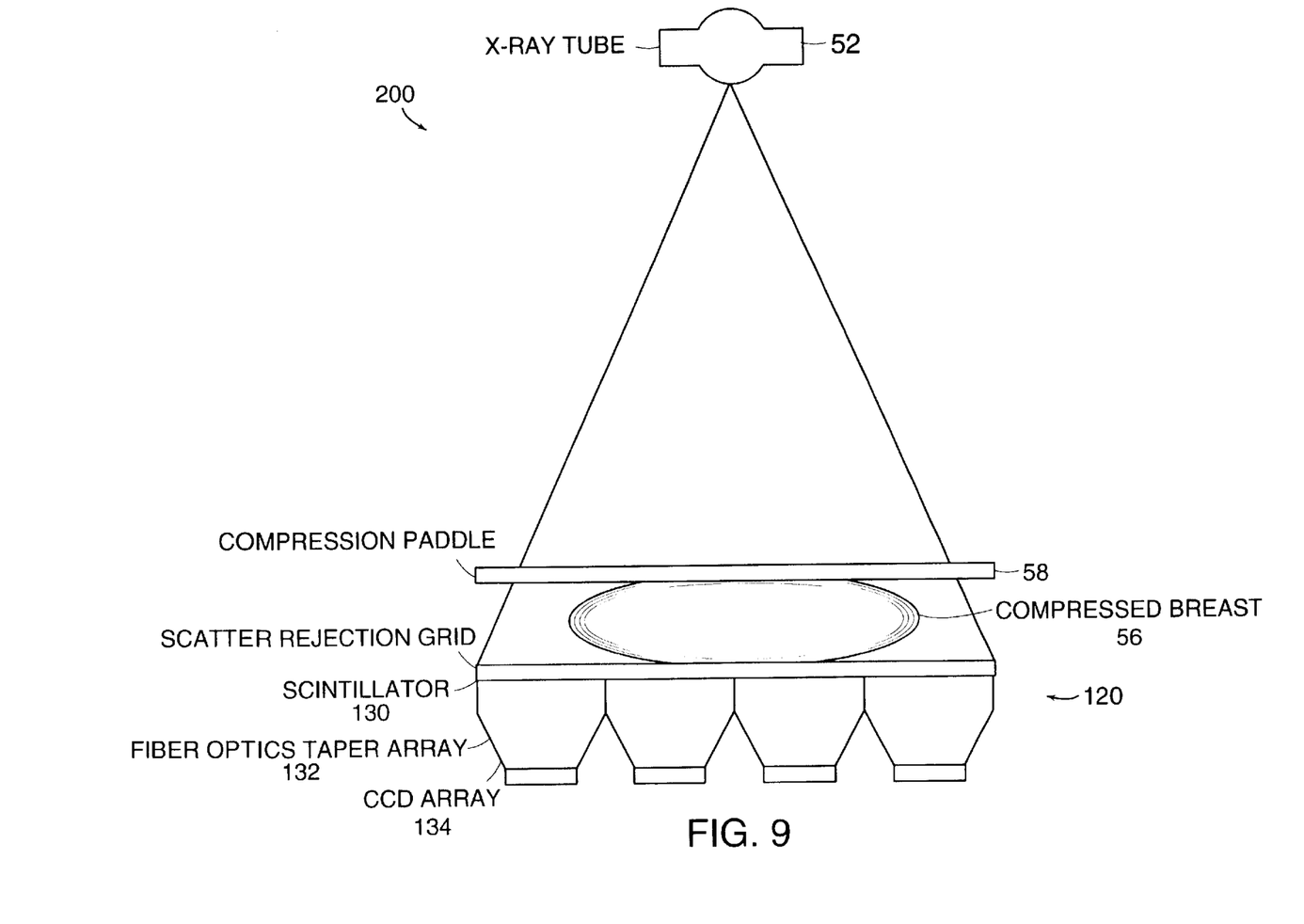
FIG. 9 illustrates the use of a preferred embodiment of a mammography machine according to the present invention.

FIG. 9 illustrates the use of a mammography machine 200 according to the present invention. A breast 56 is compressed between a compression paddle 58 and a scatter rejection grid 62 which is on top of the single exposure, large imager array 120. The array comprises of a scintillator 130, an optical system 132, and electronic imagers 134. The x-ray radiation strikes the scintillator 130, which may contain phosphor or phosphor—like material such as Tb:GdO$_2$S or CsI, which generates visible light in proportion to the intensity of the x-ray radiation striking it. The visible light enters the optical system 132 and is transmitted via optical fibers to the electronic imagers 134. The electronic imagers provide the analog image data to the receptor electronics 128, as described above.

Figure 10:
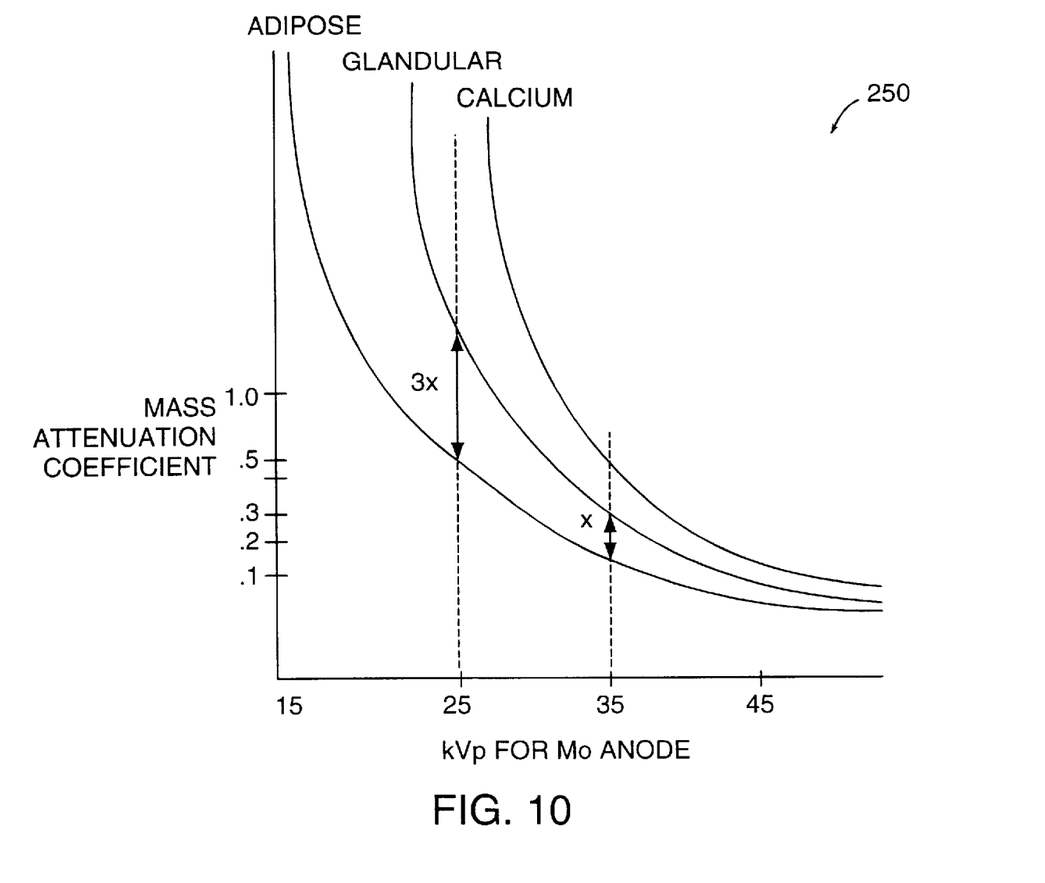
FIG. 10 is a chart illustrating contrasts between different breast tissue types over a range of kVp.

Because the breast may be imaged in a single exposure, heat loading problems are avoided. This allows the conventionally accepted Mo/Mo or Mo/Rh x-ray tube to be used at the optimum 23 kVp–28 kVp energy range. FIG. 10 is a chart 250 illustrating the approximate contrasts between adipose, glandular, and calcified tissue are greater at 25 kVp than at 37 kVp. For example, the contrast between adipose and glandular tissue is about three times as great at 25 kVp than at 35 kVp. Thus, this energy range provides better contrast between tissue types than other digital mammography machines, which typically employ tungsten x-ray tubes which operate at energy levels on the order of 40 kVp.

Because the array allows a single exposure mammogram, a digital mammography machine does not require multiple exposures to radiation, no alterations to the x-ray tube, and no need for complicated mechanical structures for scanning across a patient's breast.

3. Digital Mammography Image Processing

Figure 11:
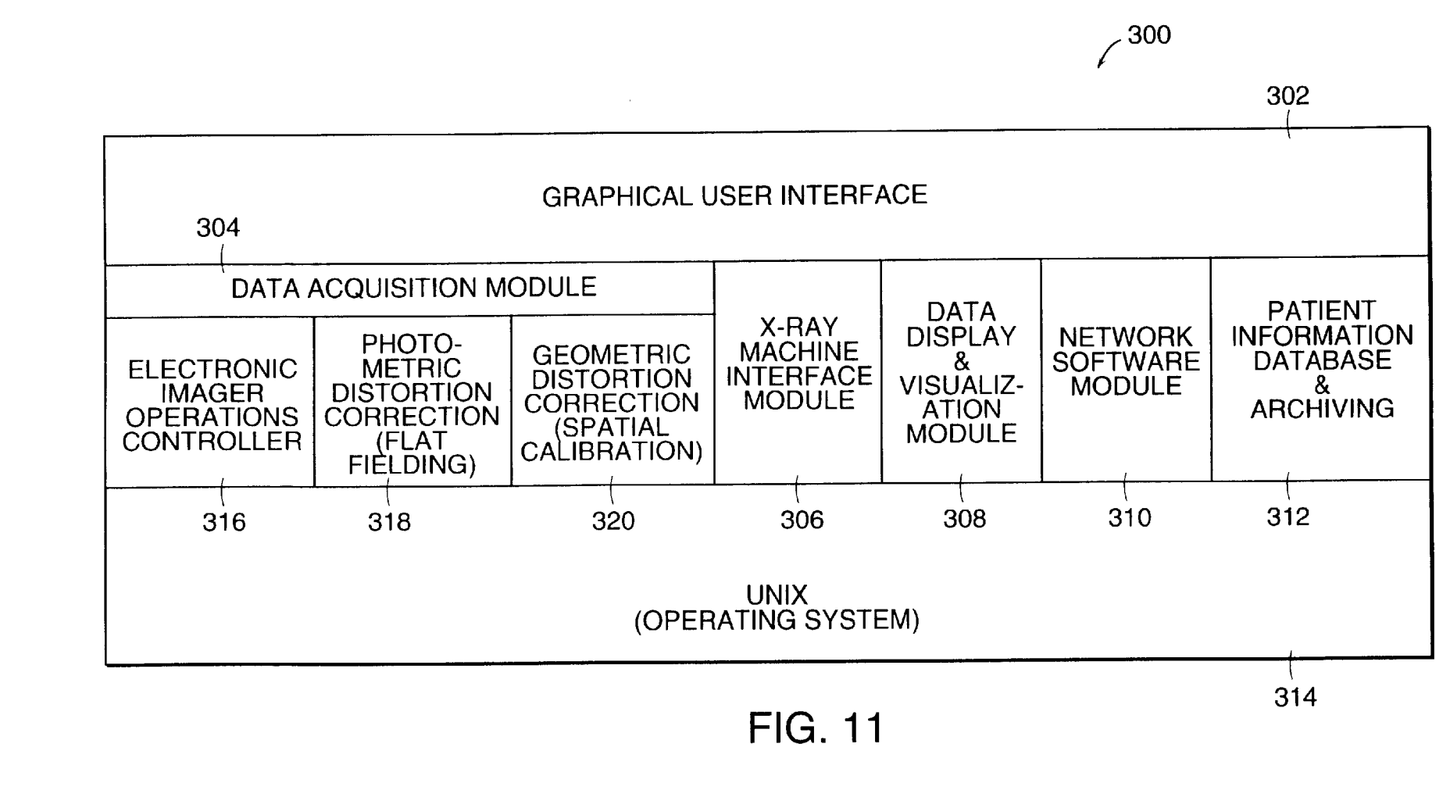
FIG. 11 illustrates a software hierarchy of a preferred image processing system according to the present invention.

FIG. 11 illustrates the software hierarchy 300 of a preferred digital mammography image processing system according to the present invention. The software may reside in the mammography machine memory 214, and preferably comprises a graphical user interface 302 based on graphics software such as X-Windows or MOTIF (both public domain software). The graphical user interface may run on top of a number of modules and databases, including a data acquisition module 304, an x-ray machine interface module 306, a data display and visualization module 308, a network software module 310, and patient information database and archiving 312. These modules and databases run on an operating system 314, such as UNIX.

The data acquisition module 304 is responsible for obtaining and processing the image data. This module includes three submodules. An electronic imager operations controller 316, a photometric distortion correction 318, and a geometric distortion correction 320. The electronic image operations controller 316 controls the electronic imagers 134 (FIG. 3B). This controller handles the electronic imager refresh, charge integration, and data read out functions. The operations controller also knows when a x-ray transmission has ended and that data is to be collected.

The photometric distortion correction 318 performs a "flat fielding" function. Flat fielding is a process to correct non-uniform responsivities of the individual detectors. Flat fielding is performed as follows. A surface having uniform transmission characteristics, such as a piece of plastic having a uniform density and thickness, is placed over the imaging array 120 (FIGS. 3A and 3B). The uniform nature of the surface suggests that each pixel should detect the same level and should have the same output. In practice, however, imperfections and other factors cause the pixels to have a slightly different values. The flat fielding process determines the amount each pixel varies from a reference level and calibrates each pixel to that reference level. This assures that imperfections in each pixel's response characteristics are accounted for.

The geometric distortion correction 320 performs spatial calibrations. Optical distortions may be caused by spatial irregularities in the optical system 132. These irregularities are corrected by a spatial calibration. A presently preferred spatial calibration method is described. A grid having known, regularly spaced dimensions is placed at the entrance aperture and imaged. The array's transfer function may be determined by comparing the known grid dimensions with the electronic output image. All images may then be corrected using this optical transfer function. A person skilled in the art recognizes that any number of processes may be used to calibrate the image.

The x-ray machine interface module 306 provides the "safety interlock" discussed above. For example, the x-ray machine interface may inform the electronic imager electronics that an x-ray transmission will be made shortly. The data display and visualization module 308 controls the brightness, contrast, zoom, and other display functions. The network software module 310 contains software which controls the network interface 226. This software connects the data to a network such as an Ethernet or TCP/IP protocol network. The patient information database and archive 312 may be optical disks (e.g., stored in disk drive 224) storing patient information, radiation dosage information, previous mammograms images, or other information.

After the image is taken, a reduced resolution image is immediately available on the technologist monitor. This allows the technologist's to ascertain proper positioning and exposure technique. Within about 10 seconds, a full resolution image is available. A preferred pixel dimension for a digital mammogram is 6400×4800 pixels. This is larger than a typical computer video monitor. Thus, the image processing software allows an entire breast image to be viewed at a reduced resolution or the viewer may zoom or pan to areas of interest.

4. A Digital Mammography Local Area Network

Figure 12:
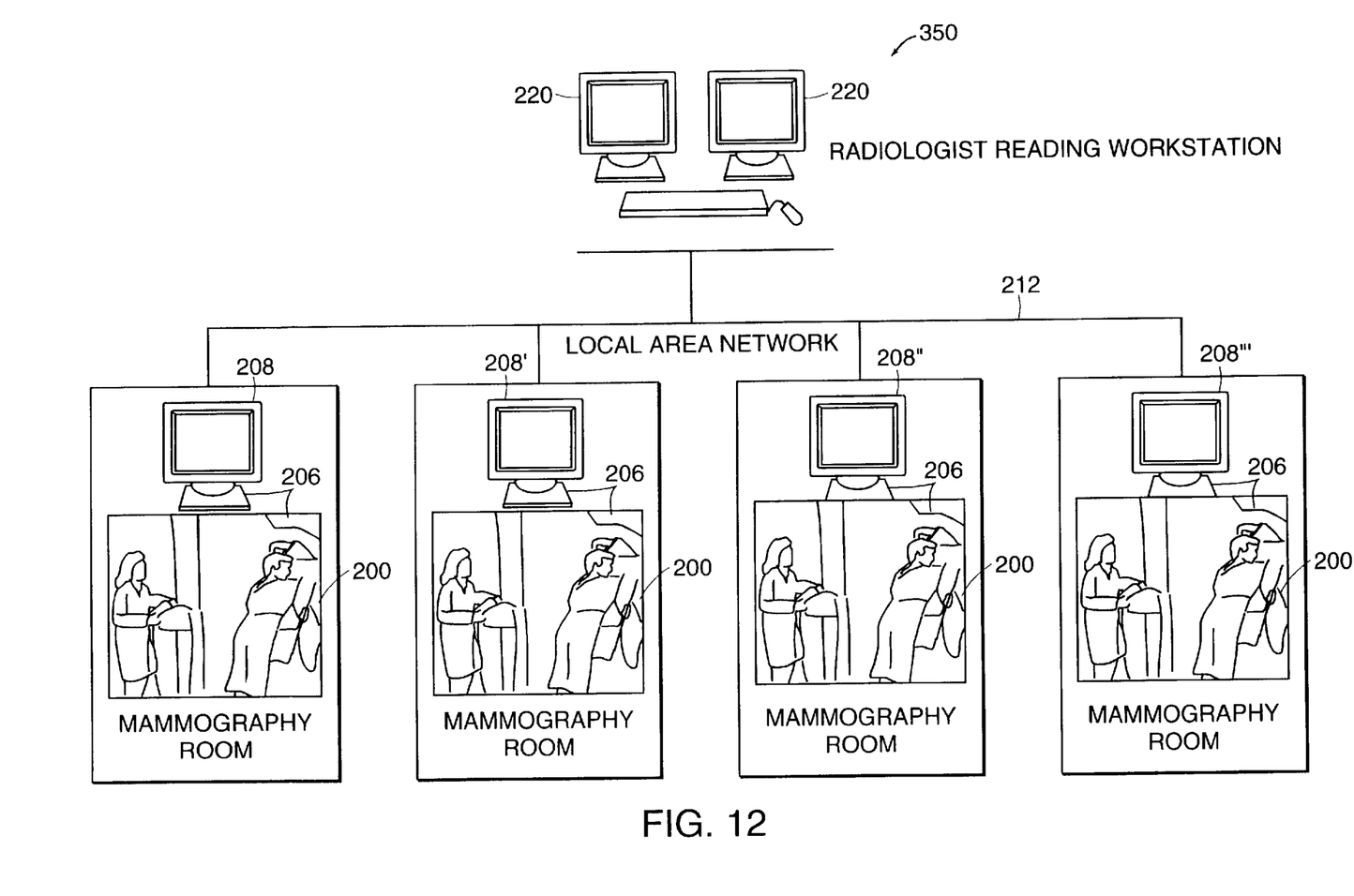
FIG. 12 illustrates a local area network comprising a number of mammography machines according to the present invention.

FIG. 12 illustrates a Local Area Network (LAN) 350 using a number of digital mammography machines 200 according to the present invention. The LAN preferably operates under a known LAN protocol, such as Ethernet or ATM. The hardware may comprise well-known network hardware, including a databus 212 such as a standard bus, such as a SCSI, S-bus, VME-bus, or PCI bus.

When an image is taken, the image is converted into digital form by the receptor electronics 128 and transmitted via the high speed serial dataline 206 to an electronics controller 208. The data may be processed by the electronics controller 208 and sent to the data bus 212. The data may then be transmitted via the bus 212 to the radiologist's work station 220. The radiologist's work station 220 may be connected to a plurality of mammography machines, as shown in FIG. 12. Preferably, the radiologist's work station has at least two gray scale monitors with high resolution (i.e., 2300×1700 pixels) and high brightness (i.e., >150 ft-lamberts). Any number of monitors may be used. For example, additional monitors may be used to view the patient's previous mammography, which may be stored in the patient database module 312.

5. Digital Mammography and Teleradiology

Figure 13:
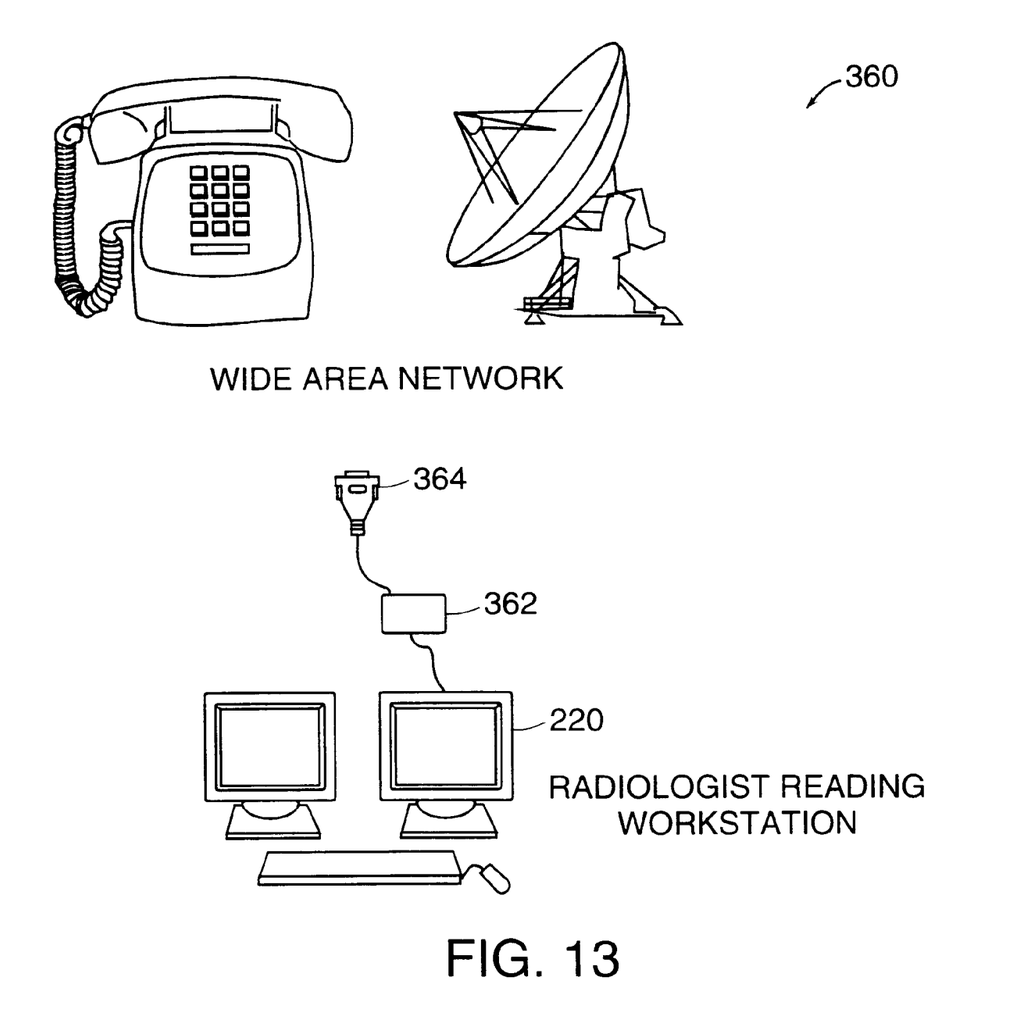
FIG. 13 illustrates a wide area network including digital mammography machines according to the present invention.

The radiologist's work station 220 may be a gateway to a wide area network (WAN). FIG. 13 illustrates a WAN 360 according to the present invention. The work station 220 may have a network module 362 and a serial port 364 connected to a communication line. The communication line may be a dedicated wide band data link, such as a T1 or T3 leased line. The wide bank data link may be established between the mammography screening/imaging area and a radiologist's or other physician's work area. A leased telephone line (i.e., a T1 line), a coaxial or fiber optic network may be established using the Ethernet, FDDI, or ATM network protocols. Thus, digital images may be transmitted over telephone lines or via satellite communications and viewed, simultaneously, if desired, by a number of persons located in different locations.

Conclusion

A large array, single exposure digital mammogram machine is provided. This device overcomes the system performance compromises of known digital mammography systems: incompatibility with existing mammography machine design, increased radiation exposure time, involuntary patient movement during prolonged imaging, heat build-up in the x-ray tubes, and higher operating energy ranges resulting in a reduced contrast between tissue types. The digital imager does not need to be developed as film does: the image may be viewed in a few seconds after the tissue has been imaged. The array may be used in a conventional mammography machine without altering the machine. The digital information may be processed, stored, transmitted, and enhanced in the same manner as other digital images. The digital image allows for a LAN or WAN to be established for remote and/or simultaneous viewing of the image.

The digital mammography machine described above provides significantly superior mammogram images. The invention has been used on patients having breast implants. The image quality has been found to be significantly better than is possible with film mammograms. Also, the increased tonal range allows radiologists to readily distinguish between microcalcifications—which do not need to be removed—and cancerous tissue—which need to be removed. This latter advantage results in avoiding unnecessary procedures to remove growths which previously could not definitely be identified as microcalcifications.

The embodiment of the invention described here is intended to be illustrative only. For example, a person skilled in the art readily understands that the invention may be used for any type of digital imaging, not just for mammography. The invention is described as a mammography device because the stringent mammography imaging requirements readily illustrate the invention's suitability to all types of radiological imaging. A person skilled in the art recognizes that the electronic imagers may be electronic devices other than CCDs. Numerous alternative embodiments may be devised by those skilled in the art without departing from the spirit and scope of the following claims.

I claim:

1. A mammography machine having an x-ray source, a breast compression plate, and an image receptor, wherein the image receptor is a digital image receptor, comprising:

a. a plurality of electronic imaging charge coupled devices arranged in a multi-dimensional array sufficiently large to image an entire breast; and b. an optical system optically coupled to a surface of each electronic imaging charge coupled device; the optical system having an image receptor surface configured to be substantially free of gaps between portions of the optical system coupled to surfaces of different electronic imaging charge coupled devices.

2. The mammography machine of claim 1, wherein the optical system comprises a fiber optic bundle configured to map to an interior of each of the electronic imaging devices.

3. The mammography machine of claim 2, wherein the optical system and electronic imaging devices are coupled in a manner that permits the plurality of electronic imaging devices to be butted together in two dimensions.

4. The mammography machine of claim 1, further comprising a multiplexer configured to multiplex pixels from each of the electronic imaging devices to provide an accurate representation of a patient's breast.

5. The mammography machine of claim 1, wherein the optical system and electronic imaging device are coupled in a manner in which pixels at edges of the electronic imaging devices are not used.

6. The mammography machine of claim 5, further comprising digital image processing electronics configured to eliminate unused pixels to convert the outputs into an accurate representation of a patient's breast.

7. The mammography machine of claim 1, wherein the electronic imaging devices are charged coupled devices.

8. The mammography machine of claim 1, further comprising digital image processing electronics connected to receive an output from each of the plurality of electronic imaging devices and configured to convert the outputs into an accurate representation of a patient's breast.

9. The mammography machine of claim 8, wherein the digital image processing electronics comprises:

a. a demultiplexer connected to the digital imager outputs;

b. a buffer connected to an output of the demultiplexer; and c. a logic circuit configured to arrange the digital outputs into an accurate image.

10. The mammography machine of claim 8, wherein the digital image processing electronics comprises:

a. a photometric distortion correction module configured to calibrate photometric properties of the digital outputs; and b. a geometric distortion correction module configured to calibrate optical distortion of the digital outputs.

11. The mammography machine of claim 1, wherein the digital image processing electronics are configured to connect to a local area network.

12. The mammography machine of claim 1, wherein the image receptor is configured as a cassette.

13. The mammography machine of claim 12, wherein the cassette has dimensions substantially the same as the dimensions of an x-ray film cassette.

14. The mammography machine of claim 1, wherein the image receptor is configured to provide a digital output.

15. A mammography machine having an x-ray source, a breast compression plate, and an image receptor, wherein the image receptor is a digital image receptor, comprising:

a. a plurality of electronic imaging charge coupled devices arranged in a multi-dimensional array sufficiently large to image an entire breast; and b. an optical system optically coupled to a surface of each electronic imaging charge coupled device; the optical system having an image receptor surface configured to be substantially free of gaps between portions of the optical system coupled to surfaces of different electronic imaging charge coupled devices; the portions of the optical system coupled to surfaces of different electronic imaging charge coupled devices having a taper intermediate the image receptor surface and the surfaces of the electronic imaging charge coupled devices.

* * * * *